(12) United States Patent
Trussardi

(10) Patent No.: US 7,531,687 B2
(45) Date of Patent: May 12, 2009

(54) PREPARATION OF OSELTAMIVIR PHOSPHATE

(75) Inventor: René Trussardi, Birsfelden (CH)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 12/284,099

(22) Filed: Sep. 18, 2008

(65) Prior Publication Data

US 2009/0076296 A1    Mar. 19, 2009

(30) Foreign Application Priority Data

Sep. 18, 2007   (EP) .................. 07116617

(51) Int. Cl.
*C07C 205/00* (2006.01)
(52) U.S. Cl. .................................... 560/125
(58) Field of Classification Search ................. 560/125
See application file for complete search history.

(56) References Cited

U.S. PATENT DOCUMENTS 6,403,824 B2    6/2002   Abrecht et al.

FOREIGN PATENT DOCUMENTS

WO    WO 98/07685         2/1998
WO    WO 98/07685 A1      2/1998

OTHER PUBLICATIONS

J. C. Rohloff et al. "Practical Total Synthesis of Anti-Influenza Drugs GS-4104", Journal of Organic Chemistry 1998 63:4545.
Peter. J. Harrington et al. "Research and Development of a Second-Generation Process for Oseltamivir Phosphate, Prodrug for a Neuroamidase Inhibitor" Organic Process Research and Development 2004 8:86-91.
C.U. Kim et al, >> Influenza neuraminidase inhibitors possessing a novel hydrophobic interaction in the enzyme active site : design, synthesis and structural analysis of carbocyclic sialic acid analogues with potent anti-influenza activity << Journal of the American Chemical Society 1997 119:681.
M. Federspiel et al., "Industrial Synthesis of the Key Precursor in the Synthesis of the Anti-Influenza Drug Oseltamivir Phosphate (Ro 64-0796/002, GS-4104-02): Ethyl (3R, 4S,5S)-3-(1-ethyl-propoxy)-cyclohex-1-ene-1-carboxylate", Organic Process Research and Development 1999 3:266.
Federspiel, M., et al., "Industrial Synthesis of the Key Precursor in the Synthesis of the Anti-Influenza Drug Oseltamivir Phosphate (Ro 64-0796/002, GS-4104-02): Ethyl (3R, 4S, 5S)-3-(1-ethyl-propoxy)-cyclohex-1-ene-1-carboxylate", *Org. Process Res. & Development*, 1999 vol. 3, pp. 266-274.
Harrington, P. J., et al. "Research and Development of a Second-Generation Process for Oseltamivir Phosphate, Prodrug for a Neuroamidase Inhibitor," *Org. Process Res. & Development* , 2004, vol. 8, pp. 86-91.
Kim, C.U., et al, "Influenza neuraminidase inhibitors possessing a novel hydrophobic interaction in the enzyme active site : design, synthesis and structural analysis of carbocyclic sialic acid analogues with potent anti-influenza activity" *Journal of the American Chemical Society*, 1997, vol. 119, p. 681.
Rohloff, J.C., et al. "Practical Total Synthesis of Anti-Influenza Drug GS-4104," *J. Org. Chem.* 1998, vol. 63, pp. 4545-4550.

*Primary Examiner*—Jafar Parsa
(74) *Attorney, Agent, or Firm*—Brian L. Buckwalter

(57) ABSTRACT

The invention provides a new process for the conversion of shikimic acid to oseltamivir (I), and optionally to an acid addition salt, via the intermediate phosphoramide VII.

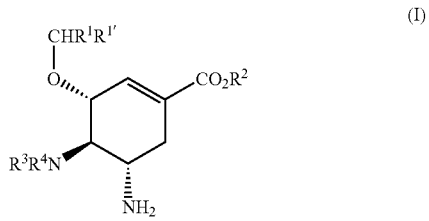

(I)

11 Claims, 1 Drawing Sheet

PREPARATION OF OSELTAMIVIR PHOSPHATE

CROSS REFERENCE TO PRIOR APPLICATIONS

This application claims the benefit of priority to EP 07116617.7 filed Sep. 18, 2007 the contents of which are hereby incorporated in their entirety by reference.

FIELD OF THE INVENTION

The present invention relates to an improved process for the preparation of Oseltamivir phosphate from shikimic acid. The process provides a new and improved route to intermediate compounds which can be convert to oseltamivir.

BACKGROUND OF THE INVENTION (3R,4R,5S)-4,5-Diamino-3-hydroxy-cyclohex-1-enecarboxylic acid derivatives of formula I, especially the (3R,4R,5S)-5-amino-4-acetylamino-3-(1-ethyl-propoxy)-cyclohex-1-ene-carboxylic acid ethyl ester and its pharmaceutically acceptable additional salts are potent inhibitors of viral neuraminidase (J. C. Rohloff et al., J. Org. Chem. 63, 1998, 45454550; WO 98/07685). Improvements to Rohloff s process have been reported. (M. Federspiel et al., Org. Proc. Res. Dev. 1999 3(4): 266-274, P. J. Harrington et al., Org. Proc. Res. Dev. 2004 8(1): 86-91) Alternatively, oseltamivir can be prepared as disclosed by S. Albrecht et al. in EP 1 127 872 published Aug. 29, 2001. New approaches for the preparation of oseltamivir have been reviewed. (M. Shibasaki and M. Kamai, Eur. J. Org. Chem. 2008 1839-1850).

There is a continuing need for improved processes to prepare oseltamivir phosphate and related derivatives of (3R,4R,5S)-4,5-diamino-3-hydroxy-cyclohex-1-enecarboxylic acid. Shikimic acid (II) [(3R,4S,5R)-3,4,5-trihydroxy-cyclohex-1-enecarboxylic acid], which can be easily obtained from biotechnological processes, e.g. genetic engineering, fermentation (Sunil S. Chandran, Jian Yi, K. M. Draths, Ralph von Daeniken, Wolfgang Weber, and J. W. Frost, Biotechnologie Progress, Vol. 19, No. 3, 2003, 808-814) is a convenient starting material. The present invention provides a new process for preparing Oseltamivir and related derivatives in good quality and yield from shikimic acid.

SUMMARY OF THE INVENTION

The present invention provides a process for the preparation of a compound of formula VII useful for the preparation of oseltamivir wherein: $R^1$, $R^{1'}$ are independently hydrogen or $C_{1-6}$ alkyl, $R^2$ is

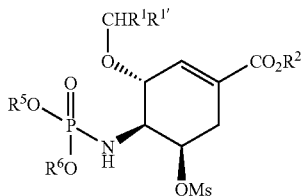

VII an $C_{1-6}$ alkyl and $R^5$ and $R^6$ are independently $C_{1-6}$ alkyl; which process comprises the steps of:

step 1—contacting an alkyl (3R,4S,5R) 3,4,5-trihydroxy-1-cyclohexene-1-carboxylate (III) wherein $R^2$ is as defined above with methanesulfonyl chloride in the presence of an aprotic organic solvent and an organic base to afford the tris-mesylate of formula IV;

step 2—contacting IV with an azide in an organic solvent, optionally in the presence of water and a phase transfer catalyst, to displace the C-3 mesyloxy-group and form V wherein $R^2$ is as defined above;

step 3—contacting V with a trialkylphosphite to reduce the azide and form the aziridine of formula VI wherein $R^2$ is as defined above and $R^5$ and $R^6$ are independently $C_{1-6}$ alkyl; and, step 4—contacting VI with a first alcohol and a Lewis acid to open the aziridine and form VII wherein $R^1$, $R^{1'}$, $R^2$, $R^5$ and $R^6$ are as defined above.

The present invention further comprises two processes to convert VII to oseltamivir and optionally to an organic addition salt.

The present invention also comprises novel compounds useful to prepare oseltamivir and optionally an acid addition salt from shikimic acid.

DETAILED DESCRIPTION OF THE INVENTION

Figure 1:
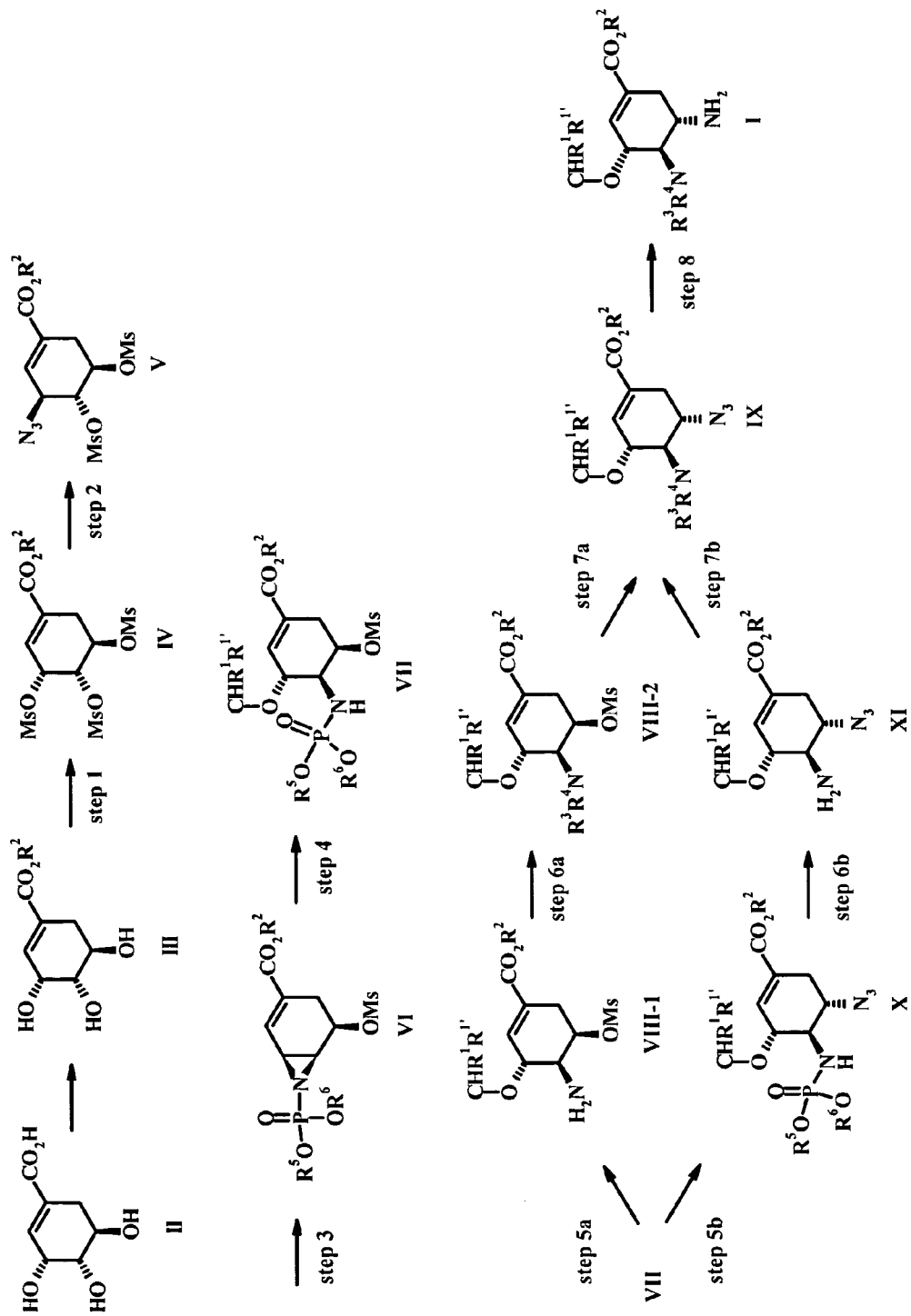
FIG. 1 depicts the process to convert a shikimate ester to a compound of formula VI and two process to further convert VI to oseltamivir (1) and optionally to an acid addition salt thereof.

The present invention affords a convenient route to (3R,4R,5S)-4,5-diamino-3-(1-ethyl-propoxy)-cyclohex-1-en-ecarboxylic acid compounds (I) which can efficiently converted to oseltamivir phosphate. The process steps in the current invention often can be carried out without the isolation and purification of the corresponding intermediates which further enhances the efficiency and overall yield of the process and thus provides a significant improvement over existing processes.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"scan be carbon, both R"scan be nitrogen, or one R" can be carbon and the other nitrogen.

When any variable (e.g., $R^1$, $R^{4a}$, Ar, $X_1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of 24 the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

As used herein, the term "treating", "contacting" or "reacting" when referring to a chemical reaction means to add or mix two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "nonpolar" or "aprotic" organic solvent means organic solvents such as diethyl ether, ligroin, pentane, hexane, cyclohexane, heptane, chloroform, benzene, toluene, dioxane, tetrahydrofuran, dichloromethane or ethyl acetate.

The term "polar aprotic solvent" means organic solvents such as formamide, N,N-dimethylformamide, dimethylsulfoxide, N-methylpyrrolidone or hexamthylphosphoramide.

The term "polar protic solvent" means organic solvents such as lower alkanols, formic acid and acetic acid. The term alcoholic solvent refers to a $C_{1-6}$ alcohol. General the first, second and third alcoholic solvent referred to herein can be independently selected and may or may not be the same. It should be apparent that the first alcoholic solvent is the moiety incorporated onto C-3 of the cyclohexane ring.

The term "ethereal solvent" means solvents such as tetrahydrofuran, dimethoxyethane, dioxane, and dialkyl ethers such as diethyl ether and methyl isobutyl ether.

The term "acylating agent" as used herein refers to either an anhydride, acid halide or an activated derivative of an N-protected alpha amino acid. The term "anhydride" as used herein refers to compounds of the general structure RC(O)—O—C(O)R wherein R is an N-protected alpha amino. The term "acid halide" as used herein refers to compounds of the general structure RC(O)X wherein X is a halogen. The term "activated derivative" is as defined below.

The term "phase transfer catalyst" as used herein refers to a quaternary ammonium salt (e.g., tetrabutyl ammonium, $[C_4H_9]_4N^+$), paired with an anion such as halogen or hydrogen sulfate. The catalyst can exchange anions and transport the anion into the organic phase. Reactivity is further enhanced because once the anion or neutral compound is in the organic phase, it has very little (if any) hydration or solvation to attenuate the reactivity.

The reduction of organic azides to amines has been effected with a variety of reagents and the term "reducing agent" includes, but is not limited to, $LiAlH_4$, $NaBH_4$, $NaBH4/CoCl_2.6H_2O$, catalytic hydrogenation, trialkyl and triaryl phosphines, trialkylphosphites, $H_2S$, diborane, $Bu_3SnH$, $Zn/HCl$, $SmI_2$, $Sm/I_2$, $Fe/NiCl_2.6H_2O$ and $Zn/NiCl_2$. The Staudinger reaction is among the mildest reducing conditions and entails treating the azide with a phosphine to form the corresponding iminophosphorane, which in the presence of water is hydrolyzed to the amine. Aqueous organic solvents can be used advantageously. References to procedures can be found in E. F. V. Scriven and K. Turnbull, *Chem. Rev.* 1988 88(2): 298-368; Fringuelli et al. *Synthesis* 2000 646-650; C. M. Marson and A. D. Hobson, In *Comprehensive Organic Functional Group Transformations*; S. V. Ley, Ed.; Pergamon-Elsevier: Oxford, U.K. 1995; Vol. 2, p. 297.

In one embodiment of the present invention there is provided a process to prepare a (3R,4S,5R)-4-(dialkoxy-phosphorylamino)-3-alkoxy-5-methanesulfonyloxy-cyclohexene-1-carboxylic acid ester derivative of formula VII($R^1$, $R^{1'}$, $R^2$, $R^5$ and $R^6$ are alkyl) which can be further transformed to oseltamivir. This embodiment comprises the steps of (step 1) converting an alkyl shikimate ester (III) to the corresponding tris-mesylate IV by reacting III with methanesulfonyl chloride in the presence of an aprotic organic solvent and an organic base; (step 2) stereoselectively displacing the mesyloxy substituent on C-3 with azide in an organic solvent optionally in the presence of water and a phase transfer catalyst to afford V; (step 3) contacting V with a trialkylphosphite in an organic solvent to induce a Staudinger reaction and provide the aziridine (VI) and (step 4) opening the aziridine by contacting VI with a Lewis acid in the presence of a first alcohol to form VII. One skilled in the art will appreciate that whereas in the experimental examples which follow, III is an ethyl ester and the triethylphosphite is used to produce a diethoxyphosphoramide VI ($R^5$ and $R^6$ are ethyl) other esters and other phosphite derivatives can be utilized interchangeably without departing from the spirit of the invention.

In a second embodiment of the present invention there is provide a process for further converting VII to oseltamivir, and optionally to the a pharmaceutically acceptable salt, which process comprises the steps of (step 1) converting an alkyl shikimate ester (M) to the corresponding tris-mesylate IV by reacting III with methanesulfonyl chloride the presence of an aprotic organic solvent and an organic base; (step 2) stereoselectively displacing the mesyloxy substituent on C-3 with azide in an organic solvent optionally in the presence of water and a phase transfer catalyst to afford V; (step 3) contacting V with a trialkylphosphite in an inert organic solvent to induce a Staudinger reaction and provide the aziridine (VI);

(step 4) opening the aziridine by contacting VI with a Lewis acid in the presence of a first alcohol to form VII; (step 5a) contacting VII with a strong acid in a second alcoholic solvent to hydrolyze of the phosphoramidate and afford the amine VIII-1; (step 6a) contacting VIII-1 with an acylating agent and a base to afford VIII-2; (step 7a) contacting V1H-2 with a azide in a second organic solvent and in the presence of a third alcohol to displace the remaining mesyloxy group to afford IX and (step 8) contacting IX with a reducing agent to afford oseltamivir (1) which is optionally converted to a pharmaceutically acceptable salt.

In a third embodiment of the present invention there is provide a process for further converting VII to oseltamivir, and optionally a pharmaceutically acceptable salt, which process comprises the steps of (step 1) converting an alkyl shikimate ester (III) to the corresponding tris-mesylate IV by reacting III with methanesulfonyl chloride the presence of an aprotic organic solvent an organic base; (step 2) stereoselectively displacing the mesyloxy substituent on C-3 with azide in an organic solvent optionally in the presence of water and a phase transfer catalyst to afford V; (step 3) contacting V with a trialkylphosphite in an inert organic solvent to induce a Staudinger reaction and provide the aziridine (VI); (step 4) opening the aziridine by contacting VI with a Lewis acid in the presence of a first alcohol to form VII; (step 5b) contacting VII with an azide in a second organic solvent an in the presence of a third alcohol to displace the remaining mesyloxy group to afford X; (step 6b) contacting X with a strong acid in a second alcoholic solvent to hydrolyze of the phosphoramidate and afford the amine XI; (step 7b) contacting VIII-I with an acylating agent and a base to afford IX and (step 8) contacting IX with a reducing agent to afford oseltamivir (I) which is optionally converted to a pharmaceutically acceptable salt.

In fourth embodiment of the present invention there is provided a process to prepare a (3R,4S,5R)-4-(dialkoxy-phosphorylamino)-3-(1-ethyl-propoxy)-5-methanesulfonyloxy-cyclohexene-1-carboxylic acid ethyl ester derivative of formula I ($R_1$, $R_{1'}$ and $R^2$ are ethyl and $R^5$ and $R^6$ are alkyl) which can be conveniently converted to oseltamivir. This embodiment comprises the steps of (step 1) converting ethyl shikimate (III, $R^2$ is ethyl) to the corresponding tris-mesylate IV ($R^2$ is ethyl) by reacting III with methanesulfonyl chloride the presence of an aprotic solvent and an organic base; (step 2) stereoselectively displacing the mesyloxy substituent on C-3 with azide in an organic solvent optionally in the presence of water and a phase transfer catalyst to afford V ($R^2$ is ethyl); (step 3) contacting V with a trialkylphosphite in an inert organic solvent to induce a Staudinger reaction and provide the aziridine VI ($R^2$ is ethyl) and (step 4) opening the aziridine by contacting VI with a Lewis acid in the presence of an 3-pentanol to form VII ($R_1$, $R_{1'}$ and $R^2$ are ethyl).

In fifth embodiment of the present invention there is provided a process to prepare a (3R,4S,5R)-4-(diethoxy-phosphorylamino)-3-alkoxy-5-methanesulfonyloxy-cyclohexene-1-carboxylic acid ester derivative of formula I ($R_1$, $R_{1'}$, $R^2$ are alkyl and $R^5$ and $R^6$ are ethyl) which can be conveniently converted to oseltamivir. This embodiment comprises the steps of (step 1) converting an alkyl shikimate ester (III) to the corresponding tris-mesylate IV by reacting III with methanesulfonyl chloride the presence of an aprotic organic solvent and an organic base; (step 2) stereoselectively displacing the mesyloxy substituent on C-3 with azide in an organic solvent optionally in the presence of water and a phase transfer catalyst to afford V; (step 3) contacting V with a triethylphosphite in an inert organic solvent to induce a Staudinger reaction and provide the aziridine (VI, $R^5$ and $R^6$ are ethyl) and (step 4) opening the aziridine by contacting VI with a Lewis acid in the presence of a first alcohol to form VII ($R^5$ and $R^6$ are ethyl).

In a sixth embodiment of the present invention there is provided a process to prepare ethyl (3R,4S,5R)-4-(diethoxyphosphorylamino)-3-(1-ethyl-propoxy)-5-methanesulfonyloxy-cyclohex-1-enecarboxylate (I, $R^1$, $R^{1'}$, $R^2$, $R^5$ and $R^6$ are ethyl) which can be conveniently converted to oseltamivir. This embodiment comprises the steps of (step 1) converting an ethyl shikimate (III, $R^2$ is ethyl) to the corresponding tris-mesylate IV by reacting EtOAc solution III with methanesulfonyl chloride in the presence TEA; (step 2) stereoselectively displacing the mesyloxy substituent on C-3 with sodium azide in anhydrous DMSO or aqueous EtOAc containing tetrabutylammonium hydrogen sulfate to afford V; (step 3) contacting a toluene solution of V with a triethylphosphite to induce a Staudinger reaction to provide the aziridine (VI, $R^2$, $R^5$ and $R^6$ are ethyl) and (step 4) opening the aziridine by contacting VI with a boron trifluoride in the presence of 3-pentanol to form VII ($R^1$, $R^{1'}$, $R^2$, $R^5$ and $R^6$ are ethyl).

In a seventh embodiment of the present invention there is provided a process to prepare oseltamivir. This embodiment comprises the steps of (step 1) converting ethyl shikimate (III, $R^2$ is ethyl) to the corresponding tris-mesylate IV by reacting an EtOAc solution III with methanesulfonyl chloride in the presence of TEA; (step 2) stereoselectively displacing the mesyloxy substituent on C-3 with sodium azide in either anhydrous DMSO or aqueous EtOAc containing tetrabutylammonium hydrogen sulfate to afford V; (step 3) contacting a toluene solution of V with a triethylphosphite to induce a Staudinger reaction and provide the aziridine (VI, $R^2$, $R^5$ and $R^6$ are ethyl); (step 4) opening the aziridine by contacting VI with a boron trifluoride in the presence of 3-pentanol to form VII; (step 5a) contacting VII with sulfinuric acid in EtOH to hydrolyze of the phosphoramidate and afford the amine VIII-1; (step 6a) contacting a solution of VIII-1 and EtOAc with acetic anhydride and TEA to afford VIII-2 (wherein $R^1$, $R^{1'}$ and $R^2$ are ethyl, $R^3$ is acetyl and $R^4$ is hydrogen); (step 7a) contacting VIII-2 with sodium azide in anhydrous DMSO and a third alcohol or aqueous EtOAc containing tetrabutylammonium hydrogen sulfate to displace the remaining mesyloxy group and afford IX and (step 8). contacting IX with tributylphosphine and EtOH to afford oseltamivir (I) which is optionally converted to a phosphate salt with phosphoric acid.

In a eighth embodiment of the present invention there is provided a process to prepare to oseltamivir. This embodiment comprises the steps of (step 1) converting an ethyl shikimate (III, $R^2$ is ethyl) to the corresponding tris-mesylate IV by reacting an EtOAc solution III with methanesulfonyl chloride in the presence of TEA; (step 2) stereoselectively displacing the mesyloxy substituent on C-3 with sodium azide in anhydrous DMSO or aqueous EtOAc containing tetrabutylammonium hydrogen sulfate to afford V; (step 3) contacting a toluene solution of V with a triethylphosphite to induce a Staudinger reaction to provide the aziridine (VI, $R^2$, $R^5$ and $R^6$ are ethyl); (step 4) opening the aziridine by contacting VI with a boron trifluoride in the presence of 3-pentanol to form VII ($R^1$, $R^{1'}$, $R^2$, $R^5$ and $R^6$ are ethyl); (step 5b) contacting a solution of VII in anhydrous DMSO and a third alcohol or aqueous EtOAc containing tetrabutylammonium hydrogen sulfate with sodium azide to displace the remaining mesyloxy group to afford X; (step 6b) contacting X with sulfuric acid in EtOH to hydrolyze of the phosphoramidate and afford the amine XI; (step 7b) contacting a solution of VIII-1 and EtOAc with a acetic anhydride and TEA to afford IX and (step 8) contacting IX with tributylphosphine and EtOH to afford oseltamivir (I) which is optionally converted to a phosphate salt with phosphoric acid.

In ninth embodiment of the present invention there is provided a compound according to formula XIIa or XIIb:

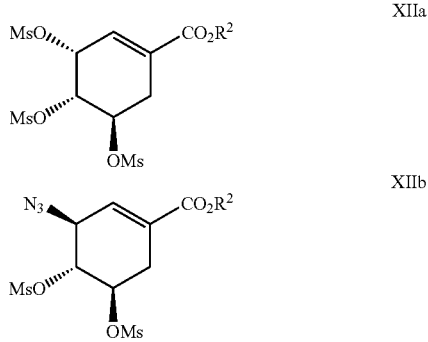

wherein $R^2$ is $C_{1-6}$ alkyl.

In a tenth embodiment of the present invention there is provided a compound according to formula XIV wherein $R^1$, $R^{1'}$ and $R^2$ are $C_{1-6}$ alkyl

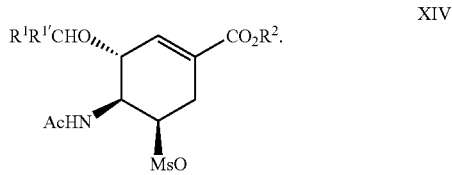

In a eleventh embodiment of the present invention there is provided a compound according to formula wherein: $R^1$, $R^{1'''}$, $R^2$, $R^5$ and $R^6$ are $C_{1-6}$ alkyl.

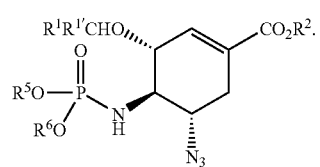

The term "alkyl" as used herein without further limitation denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-6}$ alkyl" as used herein refers to an alkyl composed of 1 to 6 carbons. Examples of alkyl groups include, but are not limited to, include methyl, ethyl, propyl, i-propyl, n-butyl, i-butyl, t-butyl or pentyl, isopentyl, neopentyl, hexyl, heptyl, and octyl.

The term "alkanoyl" as used herein denotes a group of formula —C(=O)R wherein R is hydrogen or alkyl as defined herein. The term $C_{1-6}$ alkanoyl refers to a group —C(=O)R contain 1 to 6 carbon atoms. The $C_1$ alkanoyl group is the formyl group wherein R=H and a $C_6$ acyl group refers to hexanoyl when the alkyl chain is unbranched.

The stereochemical designations α and β for a substituent in cyclic systems designates that the stereochemistry of the substituent is below or above the plane of the ring, respectively.

The term "aprotic solvent" means organic solvents such as diethyl ether, ligroin, pentane, hexane, cyclohexane, heptane, chloroform, benzene, toluene, dioxane, tetrahydrofuran, dichloromethane or EtOAc.

Abbreviations used herein include: acetyl (Ac), DMSO (DMSO), diethyl isopropyl amine (DIPEA), ethyl acetate (EtOAc), ethanol (EtOH), RT (RT or rt) and triethylamine (TEA).

Step 1 comprises formation of tris-mesylate of formula IV by reacting compound of formula III with methanesulfonyl chloride. The reaction temperature is typically in the range of −20° C. to 50° C., preferably 0° C. to 5° C.

Typically the reaction is performed as a suspension or solution of a compound of formula III, an aprotic organic solvent, preferably EtOAc, and methanesulfonyl chloride in the presence of a base. Typical bases which can be utilized include tertiary amines include but are not limited to pyridine, picoline, DMAP, TEA, tributylamine, DIPEA, N-methylmorpholine and N-methylpiperidine.

Step 2 comprises regioselective $S_N2$-substitution of the 3-mesylate-group of the tris-mesylate IV by an azide reagent to form an azide of formula V. The reaction of is typically performed in an inert organic solvent, such as DMSO, acetonitrile an ethereal solvent or with a water organic solvent mixture, preferably EtOAc and with a phase transfer catalyst, such as tetrabutylammonium hydrogen sulfate. Common azide sources include alkali metal azides, trialkylsilyl azide or tetraalkylammonium azides. The term inert organic solvent in the present context refers to a solvent which itself does not react with the mesylate or whose presence is not deleterious to the reaction. The reaction is conveniently carried out at ambient temperature.

Step 3 comprises a Staudinger reduction of the azide with a trialkylphosphite to form a iminophosphorane which displaces the adjacent mesyloxy group to afford N-diethoxyphosphoryl-aziridine (VI). (A. Hassner and J. E. Galle, *J. Am. Chem. Soc.* 1970 92(12): 3733-39; C. U. Kim et al., *J. Am. Chem. Soc.* 1997 119(4):681-90). The reaction is typically performed in an organic solvent such as toluene, alkane solvents or ethereal solvents. The reagents typically are combined at ambient temperature and the reaction warmed to between 50° C. to 150° C. depending on the solvent used.

Step 4 comprises the opening of the aziridine of formula VI in the presence of a Lewis acid catalyst and an alcohol to form a vicinal diethoxyphosphorylamino ether of formula VII. (Abrecht et al. EP 0 127 872) Typically the reagents are combined at 0-5° C. and the resulting reaction mixture is stirred at RT until the reaction is complete.

Two alternate routes have been identified to further convert VII to I. The reports differ only in the sequence steps are carried out. In steps 5a to 7a the amino group is dephosphorylated and acylated prior to introduction of the second amine as an azide substituent by $S_N2$ displacement of the remaining mesylate. In the alternative route, steps 5b to 7b, introduction of the azide is carried out first followed by dephosphorylation and acetylation of the amino substituent. Reduction of the common intermediate IX affords oseltamivir (I).

Step 5a comprises acid catalyzed hydrolysis of the phosphoramide to afford the primary amine VIII-1. Typically the reaction is performed in a suspension of compound of formula VII, an alcohol, such as EtOH and a strong acid, such as hydrochloric acid, hydrobromic acid, sulfinuric acid, phosphoric acid, methanesulfonic acid and the like, preferably sulfuric acid in an inert gas atmosphere. The reaction temperature mainly depends on the alcohol used, as a rule lies in the range of 50° C. to 150° C., preferably 80° C. to 120° C.

Step 6a comprises acylation of the liberated amine to afford the corresponding amide VIII-2. Acylation can be effected under basic conditions by using acylating agents known to the skilled in the art. The acylating agent can be an acyl halide, a carboxylic acid ester or a carboxylic acid anhydride. Suitable acylating agent include acetyl chloride or acetic anhydride. The acylation is typically run in the presence of an organic tertiary amine such as TEA or DIPEA or in an aqueous solution with an inorganic base such as $NaHCO_3$, $K_2CO_3$, or $K_3PO_4$ in water, preferably $NaHCO_3$ in water. Preferably the acylation takes place under basic conditions using a mixture of 0.5 to 2.0 equivalents of acetic anhydride in EtOAc.

Step 7a comprises displacement of the remaining methanesulfonyloxy substituent by azide to afford IX. The reaction is typically performed in an inert organic solvent, such as DMSO or a solvent mixture with DMSO and EtOH. An azide reagent, such as sodium azide is added to a solution of VIII-2 and the temperature is raised until the reaction proceeds. Typically the reaction will occur at a satisfactory rate between 80° C. to 100° C. The reaction is monitored and stopped when the starting material is consumed.

Steps 5b to 7b alter the sequence of the transformations by initially introducing the aziridine group and subsequently cleaving the phosphoramide and introducing the acetamide functionality. While the sequence differs the same general conditions are applicable.

The two alternative routes converge at azide IX. Step 8 is the final step in assembling oseltamivir and comprises reduction of the azide. While the reduction is conveniently carried out employing the Staudinger reduction with tributylphosphine, one skilled in the art will appreciate the a variety of conditions for reduction of the azide moiety are know and are within the scope of the present invention. The Staudinger reduction illustrated herein is typically carried out in a polar protic solvent such as alcohols in the presence of water. Aqueous EtOH or aqueous tetrahydrofuran can be used advantageously., preferably in, most preferably in aqueous EtOH. The reaction temperature mainly depends on the phosphine used but as a rule lies in the range of −20° C. to 30° C., preferably between 0 and 25° C. The addition of the phosphine is often completed at low temperature which is raised to complete the reduction.

In one embodiment of the invention it was found that catalytic amounts of an acid present during the reduction suppresses the ester hydrolysis which otherwise takes place to a small extent of some percent and thereby leads to an undesirable impurity. A suitable acid is a carboxylic acid, expediently acetic acid. The acetic acid is usually added in the form of glacial acetic acid in catalytic quantities of 0.5 mol % to 3.0 mol % relative to the azide of formula IX.

Work up of the reaction mixture can achieved by applying methods known to those skilled in the art. Expediently the reaction mixture is stabilized with ≦5 mol % acetic acid then concentrated in vacuo. Though I can be isolated e.g. by evaporation and crystallization, it is preferably kept in e.g. an EtOH solution and then further transformed into the pharmaceutically acceptable addition salt. The salt formation is effected with methods which are known per se and which are familiar to any person skilled in the art and in one embodiment the method described by J. C. Rohloff et al., *J. Org. Chem.* 1998 63:4545-4550; WO 98/07685) was used.

The term "pharmaceutically acceptable acid addition salts" embraces salts with inorganic and organic acids, such as hydrochloric acid, hydrobromic acid, nitric acid, sulfuric acid, phosphoric acid, citric acid, formic acid, fumaric acid, maleic acid, acetic acid, succinic acid, tartaric acid, methanesulfonic acid, p-toluenesulfonic acid, benzenesulfonic acid and the like.

Preferred pharmaceutically acceptable acid addition salt is the 1:1 salt with phosphoric acid which can be formed preferably in EtOH solution at a temperature of −20° C. to 60° C.

The starting materials and reagents used in preparing these compounds generally are either available from commercial suppliers, such as Aldrich Chemical Co., or are prepared by methods known to those skilled in the art following procedures set forth in references. Materials, reagents and the like to which reference are made in the following description and examples are obtainable from commercial sources, unless otherwise noted. General synthetic procedures have been described in treatise such as *Fieser and Fieser's Reagents for Organic Synthesis*; Wiley & Sons: New York, Volumes 1-21; R. C. LaRock, *Comprehensive Organic Transformations, 2nd edition* Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 140 and will be familiar to those skilled in the art.

The following examples illustrate the a process within the scope of the invention. This example is provided to enable those skilled in the art to more clearly understand and to practice the present invention. The specific procedures described should not be considered as limiting the scope of the invention, but merely as being illustrative and representative thereof.

EXAMPLE 1

Step 1—Preparation of (3R,4S,5R)-3,4,5-tris-methanesulfonyloxy-cyclohex-1-enecarboxylic Acid Ethyl Ester (12)

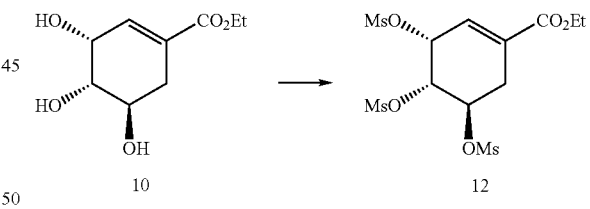

A 1000 mL two-necked round-bottom flask equipped with, a thermometer, a mechanic stirrer and an inert gas supply was charged with 20.22 g of 10 (M. Federspiel et al, *Org. Proc. Res. Dev.* 1999 3:266) and EtOAc (600 mL) was added and the resulting suspension was cooled to 0-5° C. To the suspension was methanesulfonyl chloride (24 mL) followed by dropwise addition of triethylamine (45.0 mL) over a period of 46 min, while maintaining the temperature between 0-5° C. The brown suspension was stirred for 30 min at 0-5° C., filtered over a pre cooled (0-5° C.) glass frit filter. The filter cake was washed with a total of 200 mL EtOAc, the combined filtrates were washed with 400 mL 0.5 M $H_2SO_4$, dried ($Na_2SO_4$, 100 g) and, filtered. The $Na_2SO_4$ was washed with 200 mL EtOAc and the combined filtrates evaporated in a rotary evaporator at 40° C./200-10 mbar to yield 42.24 g of 12 as a brown resin IR (ATR) 2943, 1715, 1332, 1251, 1170 cm$^{-1}$; MS (ion spray): 454.2 M+NH$_4^+$, Step 2—Preparation of (3R,4S,5R)-3-Azido-4,5-bis-methanesulfonyloxy-cyclohex-1-enecarboxylic Acid Ethyl Ester (14)

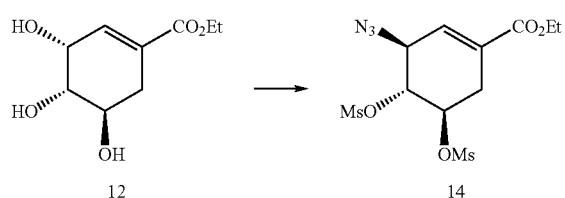

A 5 mL round-bottom flask equipped with a magnetic stirrer and an inert gas supply was charged with 436.3 mg of 12 and 0.83 mL DMSO. To the clear colorless solution at RT was added 71.5 mg sodium azide and the reaction mixture was stirred for 2.5 h, then an additional 13.7 mg of sodium azide were added and stirring continued at RT for 19 h. The reaction mixture was diluted with 5 mL of EtOAc and extracted three times with a 1 M solution of NaHCO$_3$. The organic phase was separated, dried (Na$_2$SO$_4$), filtered and evaporated at 20° C./140-10 mbar to obtain 0.33 g of the crude product as light yellow oil. The crude product was purified by SiO$_2$ column chromatography eluting with a ½ mixture of EtOAc and n-hexane. The combined fractions were evaporated and dried on a rotary evaporator to obtain 0.27 g of 14 as a colorless oil IR (ATR) 2942, 2105, 1713, 1660, 1350, 1171 cm$^{-1}$. MS (turbo spray) M+NH$_4^+$ 401.1

Step 3—Preparation of (1S,5R,6S)-7-(diethoxy-phosphoryl)-5-methanesulfonyloxy-7-aza-bicyclo[4.1.0]hept-2-ene-3-carboxylic acid ethyl ester (16)

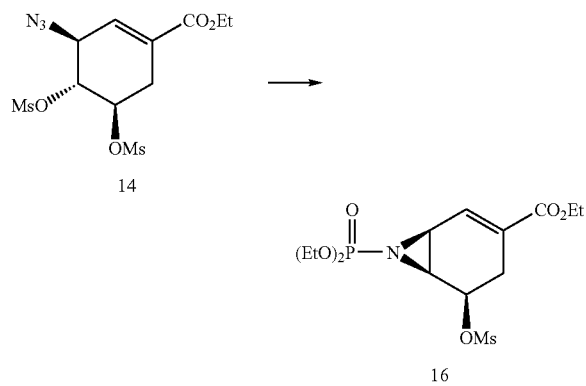

To a solution of 383.4 mg of 14 and 4.0 mL toluene in a 10 mL round-bottom flask equipped with a magnetic stirrer, a reflux condenser maintained under an argon atmosphere at RT was added, 191 µl of triethyl phosphite. Nitrogen evolution began in about 5 min and after 30 min at RT the light yellow reaction mixture was heated to reflux for 5 h, then an additional 191 µl of triethyl phosphite were added and refluxing continued for another 2 h. The reaction mixture was cooled and evaporated at 40° C./60-10 mbar to yield 470 mg of the crude product as a yellow oil. The crude product was purified by SiO$_2$ column chromatography using a 2/1 mixture of toluene and acetone. The combined fractions were evaporated and dried on a rotary evaporator 40° C./250-10 mbar to afford 87 mg of 16 as a yellow oil.

IR (ATR) 2984, 1711, 1649, 1356, 1253, 1173, 1019 cm$^{-1}$. MS (ion spray) MH$^+$ 398.0

Step 4—Preparation of (3R,4S,5R)-4-(diethoxy-phosphorylamino)-3-(1-ethyl-propoxy)-5-methane-sulfonyloxy-cyclohex-1-enecarboxylic Acid Ethyl Ester (18)

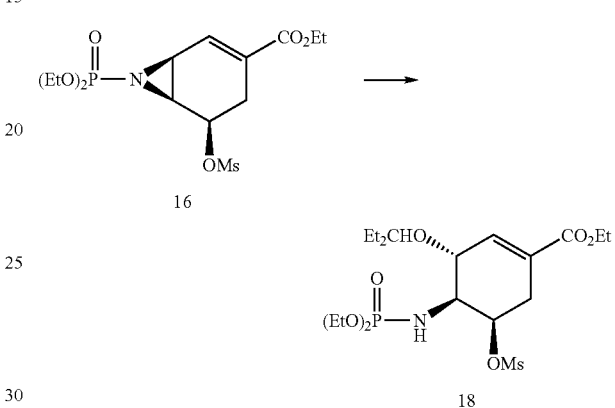

To a solution of 1.94 g of 16 and 3-pentanol (20 mL) cooled to 0-5° C. in a 50 mL round-bottom flask equipped with a magnetic stirrer and an argon gas supply was added 736 µl boron trifluoride ethyl etherate. The reaction mixture was stirred for 16 h at RT and the reaction mixture was then diluted with 50 mL of EtOAc and twice extracted with 70 mL of water. The organic phase was separated, dried (Na$_2$SO$_4$, 25 g) filtered and concentrated in a rotary evaporator at 40° C./70-10 mbar to afford 2.18 g of the crude product as a yellow oil. The crude product was purified by SiO$_2$ column chromatography eluting with tert-butyl methyl ether. The combined fractions were evaporated and dried on a rotary evaporator at 40° C./250-10 mbar to afford 1.47 g of 18 as a light yellow solid.

IR (ATR) 3236, 1711, 1246, 1024 cm$^{-1}$. MS (turbo spray) MH$^-$ 484.2

Step 5a—Preparation of (3R,4S,5R)-4-amino-3-(1-ethyl-propoxy)-5-methanesulfonyloxy-cyclohex-1-enecarboxylic Acid Ethyl Ester (20)

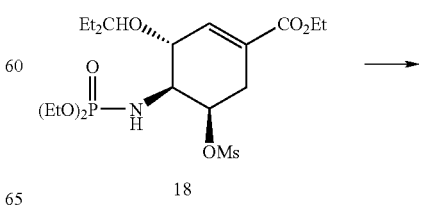

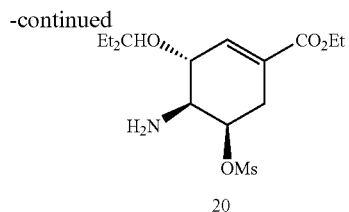

20

To a solution of 120 mg of 18 and 500 μl EtOH in a 5 mL round-bottom flask equipped with a magnetic stirrer, a reflux condenser and an inert gas supply was added 120 μl sulphuric acid (96%). The reaction mixture was refluxed for 16 h, cooled to RT and diluted with 1.0 mL of EtOAc then cooled to 0-5° C. The cooled solution was treated with 100 μl of a 28% aqueous NaOH solution and with 257 μl of a 25% aqueous NH₄OH. The well stirred mixture was diluted with 1.5 mL of water, extracted and the organic phase was separated, dried (Na₂SO₄), filtered and evaporated at 20° C./120-10 mbar and dried for 1 h at 20° C./<10 mbar to afford 56 mg of 20 as colorless oil.

IR (ATR) 1711, 1655, 1350, 1246, 1171 cm⁻¹. MS (ion spray) MH⁺350.3

Step 6a—Preparation of (3R,4S,5R)-4-acetylamino-3-(1-ethyl-propoxy)-5-methanesulfonyloxy-cyclohex-1-enecarboxylic Acid Ethyl Ester (22)

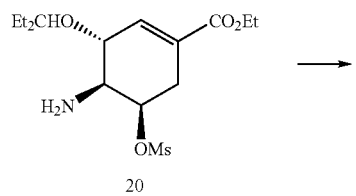

To a solution of 190 mg of 20 and EtOAc (1.6 mL) in a 10 mL round-bottom flask equipped with a magnetic stirrer and an inert gas supply was added was added at RT aqueous 1 M sodium hydrogen carbonate (1.6 mL). To the resulting mixture was added 62 μl of acetic anhydride and the 2-phase mixture was stirred for 1 h at RT. The mixture was diluted with 2.0 mL of EtOAc, the organic phase was separated, dried (Na₂SO₄), filtered and the filter cake was washed with total 3.0 mL EtOAc. The filtrate was evaporated at 40° C./200-10 mbar to afford 192 mg of 22 as off white crystals.

IR (ATR) 3303, 1714, 1648, 1534, 1344, 1251, 1174, 1094, 903 cm⁻¹. MS (ion spray) MH⁺392.0

Step 7a—Preparation of (3R,4R,5S)-4-Acetylamino-5-azido-3-(1-ethyl-propoxy)cyclohex-1-enecarboxylic Acid Ethyl Ester (24)

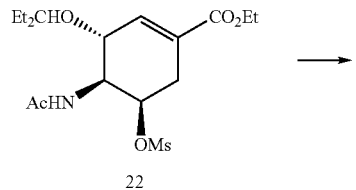

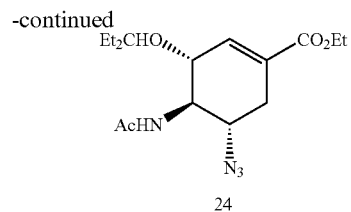

24

To a solution of 340 mg of 22, 1.2 mL of DMSO and 1.2 mL of EtOH in a 5.0 mL round-bottom flask equipped with a magnetic stirrer, a reflux condenser and an inert gas supply was added 113 mg of sodium azide and the reaction mixture was stirred for 21 h at 85-90° C. The brown reaction mixture was cooled to RT, treated with 7.0 mL of a aqueous 1 M NaHCO₃ and extracted with 7.0 mL tert-butyl methyl ether. The organic phase was dried with (Na₂SO₄), filtered and evaporated at 40° C./250-10 mbar to afford 280 mg of the crude product as brown crystals. The crude product was dissolved in 3.0 mL of tert-butyl methyl ether and stirred for 16 h at −20° C. which resulted in the formation of a beige suspension. The suspension was filtered over a pre cooled (−20° C.) glass filter frit and washed with 1.5 mL of pre cooled (−20° C.) tert-butyl methyl ether. The white crystals were dried at 40° C./10 mbar for 2 h to afford 60 mg of 24 as white crystals IR (ATR) 3265, 2101, 1713, 1659, 1559, 1249, 1078 cm⁻¹. MS (ion spray) MH⁺339.3

Step 5b—Preparation of (3R,4R,5S)-5-azido-4-(diethoxy-phosphorylamino)-3-(1-ethyl-propoxy)-cyclohex-1-enecarboxylic Acid Ethyl Ester (26)

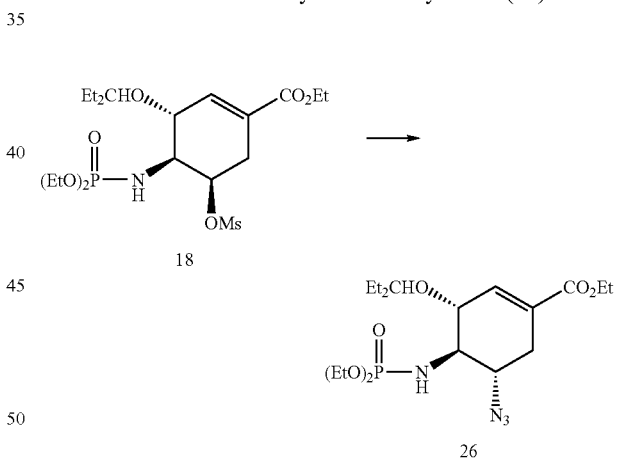

To a solution of 104 mg of 18 in 0.50 mL of EtOH and 0.50 mL of DMSO in a 5.0 mL round-bottom flask equipped with a magnetic stirrer, a reflux condenser and an inert gas supply was added 28 mg sodium azide and the reaction mixture was stirred at 85-90° C. for 20 h. The brown reaction mixture was cooled to RT diluted with 1.0 mL of EtOAc and extracted with 1.0 mL of aqueous 1 M NaHCO₃. The separated organic phase was dried (Na₂SO₄), filtered and evaporated at 40° C./120-10 mbar to obtain 40 mg of the crude product as brown crystals. The crude product was dissolved in 0.40 mL methylcyclohexane, stirred for 5 h at RT. The white crystals which formed were filtered and washed with 0.15 mL of methylcyclohexane, dried at 40° C./10 mbar for 2 h to afford 14 mg of 26 as white crystals.

IR (ATR) 3205, 2099, 1717, 1660, 1246, 1224, 1025 cm$^{-1}$.
MS (ion spray) M+OAc$^-$491.3

Step 6b—Preparation of (3R,4R,5S)-4-amino-5-azido-3-(1-ethyl-propoxy)-cyclohex-1-enecarboxylic Acid Ethyl Ester (28)

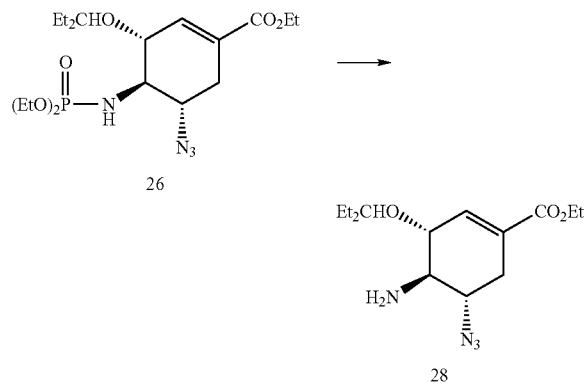

To a solution of 300 mg of 26 and 1.25 mL EtOH in a 5.0 mL round-bottom flask equipped with a magnetic stirrer, a reflux condenser and an inert gas supply was added 0.31 mL of 96% sulfuric acid. The black solution was stirred for 18 h at RT and 8 h at 80° C. The black reaction mixture was cooled to RT treated with 8.0 µL of a mixture of 65 mL ammonium hydroxide 25% and 435 mL of brine, and extracted with 9.0 mL of EtOAc. The separated organic phase was washed with 10 mL of water and the water phase was back-extracted with 9.0 mL of EtOAc. The combined organic phases were dried (Na$_2$SO$_4$, 20 g), filtered and evaporated at 40° C./140-10 mbar to afford 175 mg crude product as a dark brown oil. The crude product was purified by SiO$_2$ column chromatography eluting with EtOAc containing 1% v/v of 25% aqueous ammonium hydroxide. The combined fractions were evaporated at 40° C./140-10 mbar to afford 97 mg of 28 as a brown oil.

IR (ATR) 3393, 2098, 1713, 1241, 1070 cm$^{-1}$. MS (ion spray) MH$^+$297.2

Step 7b—Preparation of (3R,4R,5S)-4-Acetylamino-5-azido-3-(1-ethyl-propoxy)cyclohex-1-enecarboxylic Acid Ethyl Ester (30)

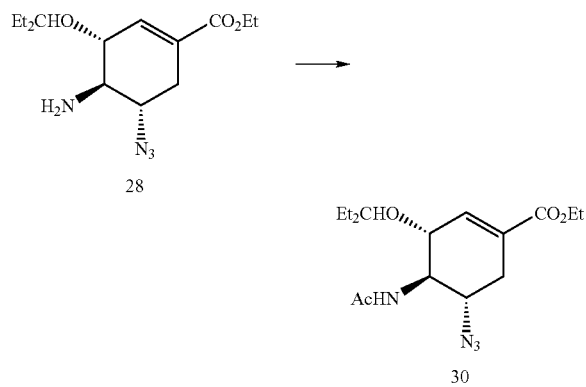

To a solution of 118.5 mg of 28 and 1.0 mL of EtOAc in a 5.0 mL round-bottom flask equipped with a magnetic stirrer and an inert gas supply was added 1.0 mL of aqueous 1 M NaHCO3. To the stirred mixture was added 45.4 µL of acetic anhydride and the mixture was stirred for 1 h at RT. The organic phase was separated and dried (Na$_2$SO$_4$, 1 g), filtered and the filter cake was washed with 2.0 mL EtOAc. The combined filtrates were evaporated at 40° C./240 to 10 mbar to afford 139 mg crude product as beige solid. The solid was suspended in 1.40 mL of n-hexane and 0.70 mL tert-butyl methyl ether, stirred for one h at RT, cooled to 0-5° C. and stirred for 2 h at 0-5° C. The suspension was filtered and the filter cake was washed with total 0.70 mL of a pre-cooled (0-5° C.) mixture of n-hexane and tert-butyl methyl ether (2/1). The filter cake was dried at 45° C./9 mbar to afford 94 mg of 30 as white crystals.

IR(NJL) 3269, 2104, 1715, 1660, 1562, 1254 cm$^{-1}$. MS (turbo spray) MH$^+$339.2.

Step 8—Preparation of (3R,4R,5S)-4-acetylamino-5-amino-3-(1-ethyl-propoxy)cyclohex-1-enecarboxylic Acid Ethyl Ester (32)

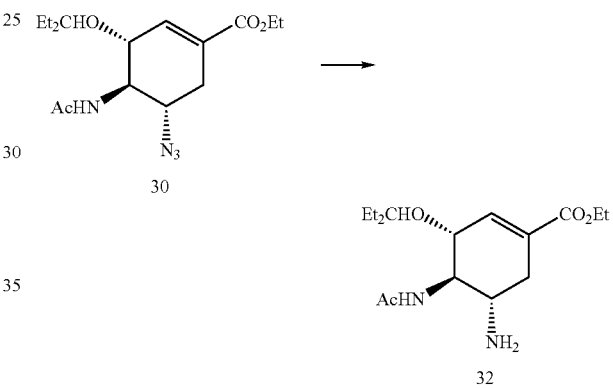

To a solution of 50.0 g (0.147 mol) of 30, 300 mL of EtOH, 50 mL of water and 0.09 g of acetic acid in a nitrogen-purged 1000 mL glass reactor fitted with a mechanical stirrer, a condenser, and a 250 mL dropping funnel was added a solution of 31.4 g (0.155 mol) of tributylphosphine in 150 mL EtOH at a temperature of 5° C. (+/−5° C.) over a period of 30-90 min. The reaction temperature was maintained at this temperature by slight cooling of the jacket (ca. 3° C.). The funnel was rinsed with 20 mL of EtOH. The clear reaction mixture was stirred for additional 90 min at 5° C. (+/−5° C.) under slight jacket cooling. Subsequently the temperature was raised within 30-60 min to 20-25° C. and the solution was stirred for another 3 h (nitrogen evolution). After the reaction was finished (HPLC assay) 0.18 g of acetic acid were added to the clear solution and the mixture was concentrated to near dryness under reduced pressure (300 to 50 mbar) at a maximum temperature of 60° C. and a maximum jacket temperature of 75° C. The oily residue (80-100 mL) was diluted with 160 mL of EtOH, the resulting solution was then again concentrated following the method described above. The oily residue was dissolved in EtOH up to a volume of 250 mL. The water content of this solution was determined by KF(Karl Fischer) titration to be less than 1.0% wt. %. Yield: 44.4 g (97% area by HPLC) of 32 in EtOH solution.

IR(NJL) 3279, 1720, 1639, 1554, 1252, 1128 cm$^{-1}$. MS (ion spray) MH$^+$313.1, MNa$^+$335.3

Preparation of (3R,4R,5S)-4-acetylamino-5-amino-3-(1-ethyl-propoxy)cyclohex-1-enecarboxylic Acid Ethyl Ester (I) Phosphate (1:1)

To a solution of 17.0 g of ortho phosphoric acid (85% in water) and 400 mL of EtOH was warmed to 50-55° C. in a dry and nitrogen purged 1000 mL glass reactor fitted with a mechanical stirrer, a condenser, and a 500 mL dropping funnel was added a solution 0.147 mol of ethyl (3R,4R,5S)-4-acetamido-5-amino-3-(1-ethylpropoxy)-1-cyclohexene-1-carboxylate (I) and 250 mL of EtOH with stirring. After fast addition (10-15 min) of two thirds (ca. 160 mL) of the total volume of this solution, the addition was stopped and the supersaturated clear solution was seeded with 0.2 g of previously obtained ethyl (3R,4R,5S)-4-acetamido-5-amino-3-(1-ethylpropoxy)-1-cyclohexene-1-carboxylate phosphate (1:1). Immediately crystallization commenced. The resulting thick suspension was stirred for 45-60 min at 5-55° C. The remaining amine solution was slowly added (45-60 min) to the suspension at 50-55° C. The feeder was rinsed with 20 mL of EtOH. Subsequently the thick suspension was continuously cooled to 12-20° C. in about 4 h (cooling speed=10° C./h). To complete the crystallization stirring was continued at 12-20° C. for additional 2±1 h. Ethyl (3R,4R,5S)-4-acetamido-5-amino-3-(1-ethylpropoxy)-1-cyclohexene-1-carboxylate phosphate (1:1) was isolated by pressure filtration (0.3 bar nitrogen overpressure, Dacron® filter cloth). The crystalline product was washed twice with 240 mL of acetone and twice with 300 mL of n-heptane at RT. Ethyl (3R,4R,5S)-4-acetamido-5-amino-3-(1-ethylpropoxy)-1-cyclohexene-1-carboxylate phosphate (1:1) was dried in vacuo (ca. 20 mbar) at a maximum temperature of 50° C. until constant weight. Yield: 54-55 g (88-91%) of the title product in the form of colorless needles with an assay of =99 wt. % (sum of impurities <0.5 wt. %, single impurities ≦0.1 wt. %).

IR(NJL) 3352, 3164, 2923, 2854, 1724, 1663, 1551, 1463, 1263, 1132 cm$^{-1}$. MS (ion spray) MH$^+$ 313.1, MNa$^+$ 335.3

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

I claim:

1. A process for the preparation of a compound of formula VII useful for the preparation of oseltamivir wherein:

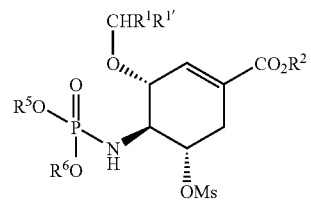

VII $R^1$ and $R^{1'}$ are independently hydrogen or $C_{1-6}$ alkyl,
$R^2$ is an $C_{1-6}$ alkyl and
$R^5$ and $R^6$ are independently $C_{1-6}$ alkyl and OMs is mesylate which process comprises the steps of:

step 1—contacting an alkyl (3R,4S,5R) 3,4,5-trihydroxy-1-cyclohexene-1-carboxylate (III) wherein $R^2$ is as defined above with methanesulfonyl chloride in the presence of an aprotic organic solvent and an organic base to afford the tris-mesylate of formula IV;

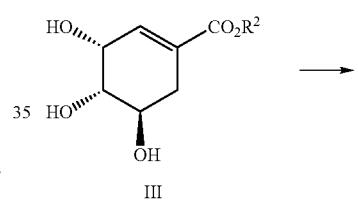

III

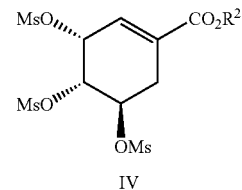

IV step 2—contacting IV with an azide in an organic solvent, optionally in the presence of water and a phase transfer catalyst, to displace the C-3 mesyloxy-group and form V wherein $R^2$ is as defined above;

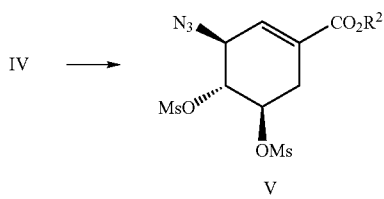

V step 3—contacting V with a trialkylphosphite in an organic solvent to reduce the azide and form the aziridine of formula VI wherein $R^2$ is as defined above and $R^5$ and $R^6$ are independently $C_{1-6}$ alkyl;

V →  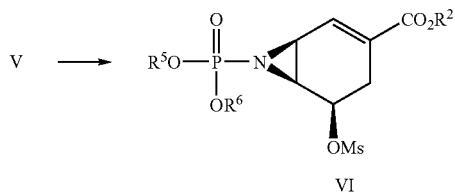

step 4—contacting VI with a first alcohol solvent and a Lewis acid to open the aziridine and form VII wherein $R^1$, $R^{1'}$, $R^2$, $R^5$ and $R^6$ are as defined above.

2. A process for the preparation of oseltamivir (I) according to claim 1, which process further comprises the steps of:

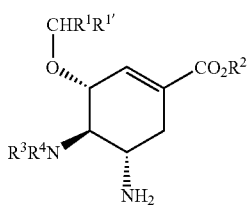

step 5a—contacting the phosphoramide of formula VII with a second alcohol solvent and a strong acid to hydrolyze the phosphoramide and form a compound of formula VIII-1 wherein:

VII → 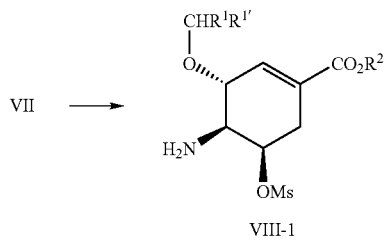

$R^1$ and $R^{1'}$ are independently hydrogen or $C_{1-6}$ alkyl and $R^2$ is an $C_{1-6}$ alkyl;

step 6a—contacting VIII-1 in an aprotic organic solvent with an acylating agent and a base to form a compound of formula VIII-2 wherein $R^3$ is $C_{1-6}$ alkanoyl and $R^4$ is hydrogen, $R^1$ and $R^{1'}$ are independently hydrogen or $C_{1-6}$ alkyl and $R^2$ is an $C_{1-6}$ alkyl;

VIII-1 → 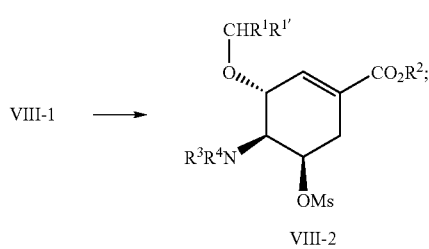

step 7a—contacting VIII-2 with an azide in a second organic solvent and a third alcohol under conditions sufficient to displace the mesylate and produce a compound of formula IX;

VIII-2 → 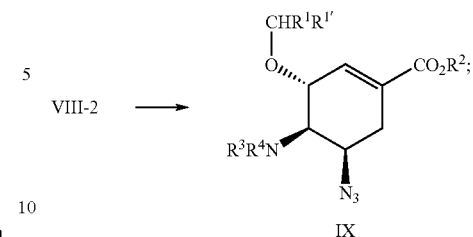

step 8—contacting IX with a reducing agent to form I and optionally contacting I with pharmaceutically acceptable acid to form an acid addition salt.

3. A process for the preparation of oseltamivir (I) according to claim 1, which process further comprises the steps of:

step 5b—contacting VII with an azide in a second organic solvent and a third alcohol under conditions sufficient to displace the mesylate and produce a compound of formula X VII → 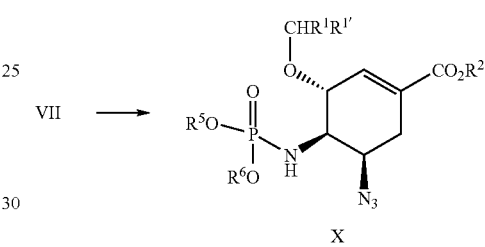

wherein $R_1$, $R^{1'}$ are independently hydrogen or $C_{1-6}$ alkyl, $R^2$ is an $C_{1-6}$ alkyl and $R^3$, $R^4$ are independently hydrogen or $C_{1-6}$ alkanoyl;

step 6b—contacting the phosphoramide of formula X with a second alcohol solvent and a strong acid to hydrolyze the phosphoramide and form a compound of formula XI wherein $R^1$, $R^{1'}$ are independently hydrogen or $C_{1-6}$ alkyl, $R^2$ is an $C_{1-6}$ alkyl X → 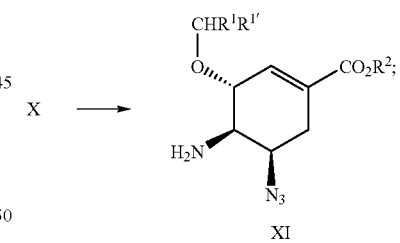

step 7b—contacting XI in an aprotic organic solvent with an acylating agent and a base to form a compound of formula IX wherein $R^1$ and $R^{1'}$ are independently hydrogen or $C_{1-6}$ alkyl, $R^2$ is an $C_{1-6}$ alkyl, $R^3$ is $C_{1-6}$ alkanoyl and $R^4$ is hydrogen;

XI → 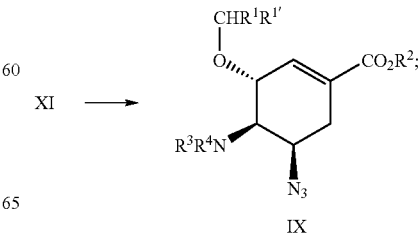

step 8—contacting IX with a reducing agent to form I and optionally contacting I with a pharmaceutically acceptable acid to form an acid addition salt.

4. A process according to claim 1, wherein $R^1$, $R^{1'}$ and $R^2$ are ethyl.

5. A process according to claim 1, wherein $R^5$ and $R^6$ are ethyl.

6. A process according to claim 1 wherein in step 1 wherein said aprotic organic solvent is EtOAc and said organic base is TEA; in step 2, said azide is sodium azide, said organic solvent is either anhydrous DMSO or aqueous EtOAc and said phase transfer catalyst is tetrabutylammonium hydrogen sulfate; in step 3, said trialkylphosphite is triethylphosphite and said organic solvent is toluene; and in step 4, said first alcohol solvent is 3-pentanol and said Lewis acid is boron trifluoride ethyl etherate.

7. A process according to claim 2 wherein in step 1 wherein said aprotic organic solvent is EtOAc and said organic base is TEA; in step 2, said azide is sodium azide, said organic solvent is either anhydrous DMSO or aqueous EtOAc and said phase transfer catalyst is tetrabutylammonium hydrogen sulfate; in step 3, said trialkylphosphite is triethylphosphite and said second organic solvent is toluene; and in step 4, said first alcohol solvent is 3-pentanol and said Lewis acid is boron trifluoride ethyl etherate, in step 5a said second alcoholic solvent is EtOH and said strong acid is sulfuric acid; in step 6a said acylating agent is acetic anhydride, said aprotic organic solvent is EtOAc and said base is TEA; in step 7a said azide is sodium azide and said second organic solvent is DMSO and said third alcohol is EtOH; in step 8 said reducing agent is tributylphosphine and said solvent is EtOH; and, said pharmaceutically acceptable acid is phosphoric acid.

8. A process according to claim 3 wherein in step 1 wherein said aprotic organic solvent is EtOAc, and said organic base is TEA; in step 2, said azide is sodium azide, said organic solvent is either anhydrous DMSO or aqueous EtOAc and said phase transfer catalyst is tetrabutylammonium hydrogen sulfate; in step 3, said trialkylphosphite is triethylphosphite and said organic solvent is toluene; and in step 4, said first alcohol solvent is 3-pentanol and said Lewis acid is boron trifluoride ethyl etherate, in step 5b said azide is sodium azide and said second organic solvent is DMSO and said third alcohol is EtOH; in step 6b said second alcoholic solvent is EtOH and said strong acid is sulfuric acid; in step 7b said acylating agent is acetic anhydride, said base is TEA and said aprotic organic solvent is EtOAc; in step 8 said reducing agent is tributylphosphine; and said pharmaceutically acceptable acid is phosphoric acid.

9. A compound according to formula XIIa or XIIb:

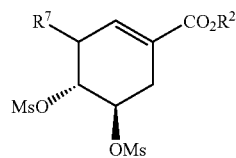

XIIa: $R^7$=α-MsO—; $R^2$ is $C_{1-6}$ alkyl wherein OMs is mesylate

XIIb: $R^7$=β-$N_3$—; $R^2$ is $C_{1-6}$ alkyl.

10. A compound according to formula XIV wherein:

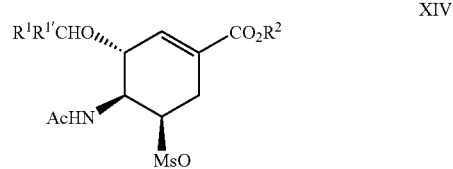

wherein $R^1$, $R^{1'}$ and $R^2$ are $C_{1-6}$ alkyl; wherein OMs is mesylate.

11. A compound according to formula XV wherein:

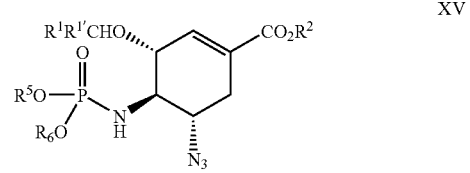

wherein $R^1$, $R^{1'}$, $R^2$, $R^5$ and $R^6$ are $C_{1-6}$ alkyl.

* * * * *